United States Patent
Skubal et al.

[19]

[11] Patent Number: 6,006,856
[45] Date of Patent: Dec. 28, 1999

[54] STETHOSCOPE SHEATHING SYSTEM

[76] Inventors: John A. Skubal, 11319 Hemlock; Richard Beamon, W. 115th Pl., both of Overland Park, Kans. 66210; Mark Holcomb, 14905 Caemen La., Olathe, Kans. 66062

[21] Appl. No.: 09/082,595

[22] Filed: May 21, 1998

[51] Int. Cl.$^6$ ...................................................... A61B 7/02
[52] U.S. Cl. ............................................................ 181/131
[58] Field of Search .................................... 181/131, 137; 381/67; 600/528

[56] References Cited

U.S. PATENT DOCUMENTS

| | | |
|---|---|---|
| 4,461,368 | 7/1984 | Plourde et al. . |
| 4,589,149 | 5/1986 | Bassi . |
| 4,757,381 | 7/1988 | Cooper, et al. . |
| 4,867,268 | 9/1989 | Ulert . |
| 4,871,046 | 10/1989 | Turner . |
| 4,995,473 | 2/1991 | Packard . |
| 5,228,851 | 7/1993 | Burton . |
| 5,269,314 | 12/1993 | Kendall et al. . |
| 5,466,898 | 11/1995 | Gilbert et al. ........................ 181/131 |
| 5,486,659 | 1/1996 | Rosenbush ............................ 181/131 |
| 5,539,162 | 7/1996 | Tuttle .................................... 181/131 |
| 5,564,431 | 10/1996 | Seward .................................. 600/528 |
| 5,623,131 | 4/1997 | Earnest ................................. 181/131 |

OTHER PUBLICATIONS

Occupational Exposure to Bloodborne Pathogens, 1996 (Revised), OSHA 3127, U.S. Department of Labor, Occupational Safety and Health Administration.

Bloodborne Pathogens and Acute Care Facilities, 1995 (Revised), OSHA 3128, U.S. Department of Labor, Occupational Safety and Health Administration.

Occupational Exposure to Bloodborne Pthogens: Precautions for Emergency Responders, 1992 (Reprinted), OSHA 3130, U.S. Department of Labor, Occupational Safety and Health Administration.

Consolidated Plastics Company Inc. (Brochure), p. 11.

Mark A Marinella, M.D. et al. *The Stethoscope—A Potential Source of Infection,* ARCh Internal Medicine, Apr. 14, 1997, pp. 786–790, vol. 157.

*Primary Examiner*—Khanh Dang
*Attorney, Agent, or Firm*—Lathrop & Gage LC

[57] ABSTRACT

An elastic sheath and a retaining ring is provided for a stethoscope having a head, a sound tube and an earpiece. The sheath has an open end for admittance of the head and a portion of the sound tube and a closed end. The sheath is sized such that the head of the stethoscope and at least a portion of the sound tube is enveloped by the sheath. The retaining ring is mounted to the sound tube and extends radially outwardly therefrom. The retaining ring is sized such that the sheath plastically deforms to envelop the retaining ring. The retaining ring thus releasably retains the sheath on the stethoscope.

9 Claims, 2 Drawing Sheets

STETHOSCOPE SHEATHING SYSTEM

BACKGROUND OF THE INVENTION

1. Field of Invention

The present invention relates to a sheathing system for a medical stethoscope and, more particularly, to a disposable sheath for the head and a portion of the tubing of a stethoscope and a retaining ring to secure the sheath to the stethoscope in order to maintain hygienic conditions and to prevent both the contamination of the patient's skin by the stethoscope and the contamination of the stethoscope by the patient's skin.

2. Statement of the Art

The stethoscope is a clinical, diagnostic instrument for performing mediate auscultation. The stethoscope is used during examination of patients in a doctor's office, in hospital clinics, emergency rooms or while conducting hospital rounds. By means of this instrument the respiratory, cardiac, plural, arterial and other sounds are conveyed to the ear of the user by applying the head of the stethoscope to the patient's chest, abdomen, and other areas. These areas may be secreting bodily fluids contaminated with infectious agents, including viruses such as the human immunodeficiency virus (HIV) resulting in the contamination of the stethoscope head and portion of the tubing in contact with the skin. Obviously, the stethoscope will contaminate the next patient's skin unless the stethoscope is sterilized between each examination.

In practice, however, medical personnel do not sterilize the stethoscope between examinations of different patients, especially during hospital rounds or busy situations. Physicians and nurses generally use their own stethoscopes without specific preventative measures. For example, it is common, after examining a patient, merely to wipe the stethoscope with a paper towel alone or with alcohol. Even if sterilization is practiced, it is very hard to clean crevices and surfaces of the stethoscope with alcohol or other conventional liquid disinfectants.

The prior art teaches the use of sheaths for covering stethoscopes to prevent cross-contamination. For example, U.S. Pat. No. 5,486,659 discloses a stethoscope protection device for protecting the stethoscope from contamination during a stethoscopic examination. It teaches the use of a decreased or stepped-down portions in the interior of the sleeve to receive the head of the stethoscope and thereby secure the sleeve on the stethoscope.

U.S. Pat. No. 5,466,898 is directed to a stethoscope isolation system for preventing nosocomial infection. The system includes a stethoscope sleeve having an adhesive strip on one side. The sleeve is adapted to envelop the entire tube and the adhesive strip is used to secure the sleeve around the tube separation area.

U.S. Pat. No. 5,539,162 discloses a cover for a stethoscope to cover the portion of tubing that will contact the carrier's neck as carried about the neck. The sleeve is retained on the stethoscope through drawstrings to allow a knot to gather the material at each end of the sound tube. Alternatively, this patent discloses the use of hook and loop material on the inside of the sleeve to fasten the sleeve between the diverging ear tubes.

The prior art contemplates sheathing the stethoscope for prevention of transmission of invective infective disease via contact with the head. However, a need exists for a system of sheathing the stethoscope that incorporates a retaining system that easily, economically and releasably retains the sheath on the stethoscope, without the need to specially fabricate standard sheaths for this purpose.

SUMMARY OF THE INVENTION

It is an object of the present invention to provide a system for preventing the transmission of infection from one patient to another via a contaminated stethoscope.

It is another object of the present invention to provide a sheathing system that securely retains the sheath in a taut relation to the stethoscope head and not interfere with the stethoscope's operation.

It is another object of the present invention to provide a sheathing system that is effective, inexpensive to manufacture, disposable and easy to implement.

These and other objects are obtained by the present invention, which generally comprises the combination of an elastic sheath for a stethoscope having a head, a sound tube and an earpiece, and a retaining ring for releasably retaining the sheath on the stethoscope. The sheath has an open end for admittance of the head and a portion of the sound tube, and a closed end. The sheath is sized such that the head of the stethoscope and at least a portion of the sound tube is enveloped by the sheath. The retaining ring is mounted to the sound tube of the stethoscope and extends radially outwardly from the sound tube. The retaining ring is sized such that the sheath plastically deforms to envelop the retaining ring and as such, the retaining ring releasably retains the sheath on the stethoscope.

DETAILED DESCRIPTION OF THE INVENTION

Figure 1:
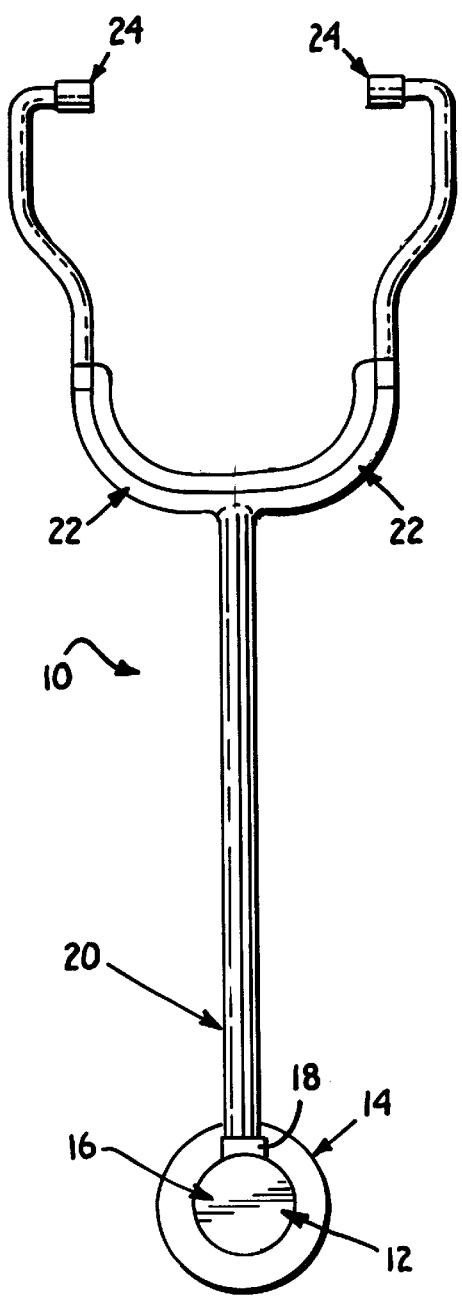
FIG. 1 is a frontal view of an exemplary off-the-shelf stethoscope
Figure 2:
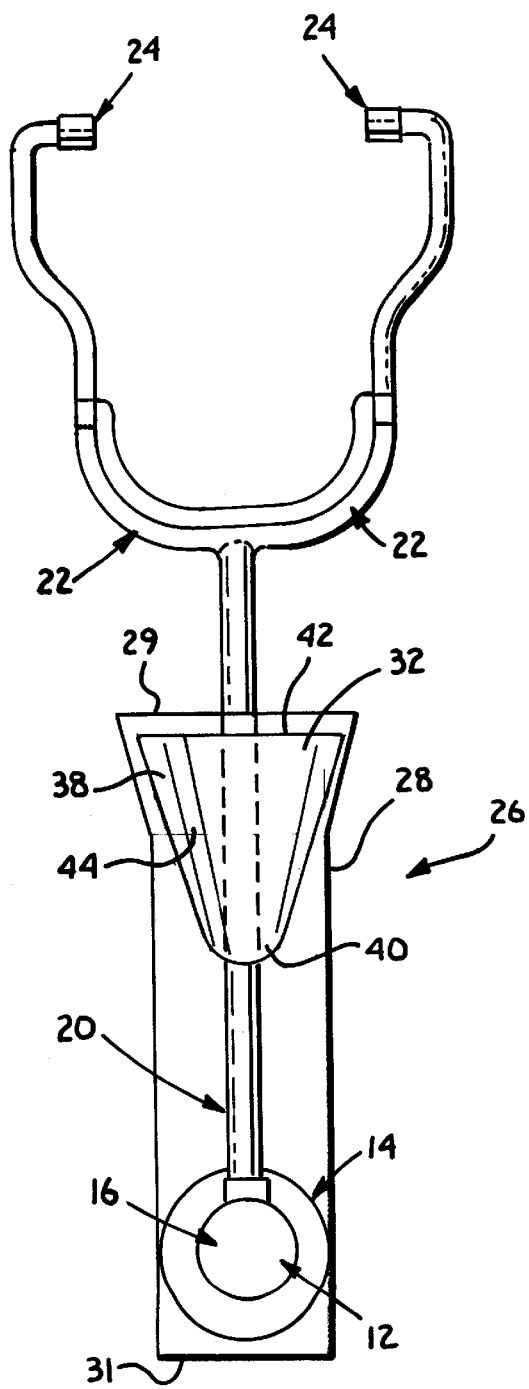
FIG. 2 is a frontal view of the sheathing system of the present invention mounted to the stethoscope.
Figure 3:
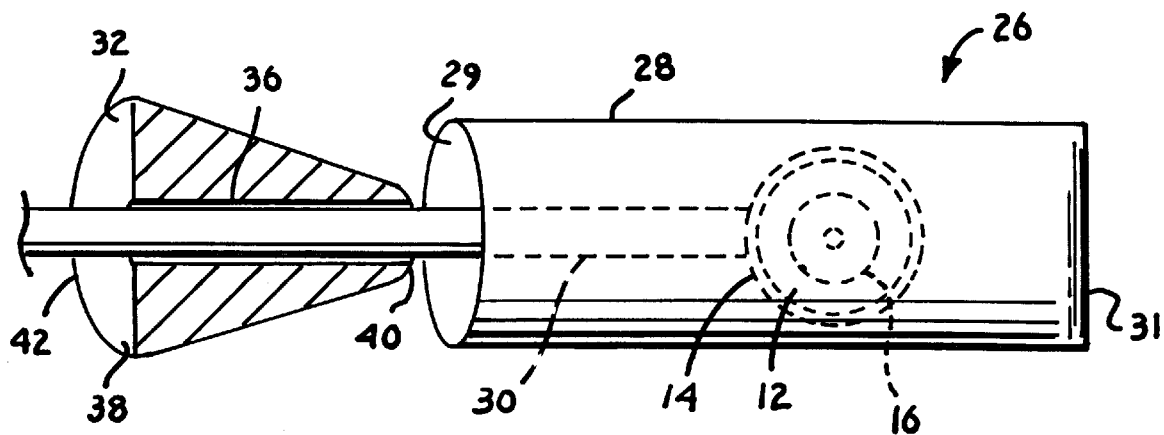
FIG. 3 is a perspective view of the sheath enveloping the head of the stethoscope, with a portion of the retaining ring cut-out.

Referring now to FIG. 1, a standard stethoscope 10 is shown to include a head 12 having a diaphragm portion 14, a bell portion 16 and a tubular outlet 18 containing an air column. A flexible sound tube 20 connects the outlet 18 to the binaural earpiece tubes 22 and ear tips 24. As shown in FIG. 2, the sheathing system, indicated generally at 26, comprises a disposable sheath 28 configured to envelop the head 12 of the stethoscope and at least a portion 30 of the sound tube 20, and a retaining ring 32 mounted to the sound tube for releasably retaining the sheath on the stethoscope 10.

The sheath 28 is preferably tubular in shape and includes an open end 29 and a closed end 31. The open end 29 is sized to receive the head 12 and the sheath is sized to extend and receive a portion 30 of the sound tube of the stethoscope. The dimensions of the sheath 28 may be somewhat variable as long as the sheath is appropriate for receiving the head 12 of a stethoscope. Preferably, a standard, nonlubricated prophylactic is used as the sheath of the present invention. As such, the sleeve is approximately two to eight centimeters in width and five to thirty centimeters in length. The sheath is preferably made of a thin, flexible, polymeric material such as polyethylene, latex rubber, silicone, soft vinyl, urethane, and the like as is well known in the art. The sheath of the present invention is simple to use and easy to manufacture with standard plastic or latex-rubber manufacturing technology.

The polymeric sheath material preferably has a thickness of from about 0.1 to 5 mils (i.e., between 0.0001 and 0.005 inches), more preferably between about 0.5 mils and 2 mils. The sheath material must be impermeable to bodily fluids. A polymeric material of such thickness does not significantly impede or degrade the fidelity of sound transmission to the stethoscope. While the sheath 28 of the present invention does not have to be sterile, sheaths may be provided, using any suitable sterilization method known for disposable, plastic medical or surgical supplies (e.g., radiation, ethylene oxide, etc.).

The retaining means of the present invention preferably comprises a retaining ring 32 mounted to the sound tube 20 of the stethoscope. The retaining ring 32 is preferably a generally cylindrical body with an interior channel 36 being configured to snugly receive a portion of the sound tube 20 of the stethoscope. The exterior surface 38 of the retaining ring 32 is generally conically shaped to taper outwardly from the end 40 nearest the head of the stethoscope to the end 42 nearest the binaural tubes 22. With this configuration, the sheath 28 may easily be extended over the retaining ring 32 with the increasing circumference of the retaining ring plastically deforming the sheath.

The ring 34 further includes a channel 44 extending from the interior passage 46 of the cylindrical ring to the exterior and extends the entire length of the retaining ring. This channel 44 permits the retaining ring to be mounted to the sound tube 20 by accepting the sound tube through the channel. It is to be understood that the retaining ring may be fabricated from any suitable material and may be closed about the sound tube in any other fashion, such as by hook and loop material without departing from the scope of the present invention.

The retaining ring 32 is preferably fabricated from a resilient material such as polyethylene, latex rubber, and the like. A resilient material is preferred so that the retaining ring can plastically deform to accept the sound the through its channel. As the sound tube enters the interior of the ring, the resilient retaining ring snaps back into place.

The retaining ring 32 is configured to extend radially outwardly from the sound tube 20 as mounted on the sound tube. The retaining ring is sized such that the sheath 28 must plastically deform to envelop the retaining ring. In this manner, the retaining ring releasably retains the sheath on the stethoscope.

In an alternative embodiment, the jacket of the sound tube is fabricated such that for a portion of the sound tube the jacket is enlarged. This enlarged portion extends radially outwardly farther than the remaining portion of the sound tube. This enlarged jacket thus functions as a retaining ring. The jacket is made of a vinyl or plastic coating. A portion of the sound tube is fabricated to have a greater thickness than the remainder of the sound tube. This portion of the sound tube is sized such that the sheath 28 must plastically deform to envelop it. In this manner, the enlarged portion of the sound tube releasably retains the sheath on the stethoscope.

Preferably the sheathing system of the present invention includes a stethoscope sheath dispenser, indicate generally at 48 for mounting a sheath 28 on a stethoscope. The dispenser 48 includes a plurality of stackable supports 50. Each support has an aperture 52 defined therethrough with the aperture being sized such that at least the head 12 of the stethoscope 10 can progress through the aperture. Each support 50 is further frustro-conically shaped such that it has a narrow end 54 defining a narrow aperture 56 and a large end 58 defining a large aperture 60. The narrow aperture 56 is sized such the elastic sheath 28 must be elastically deformed to surround the narrow end 54 of each support 50. As such, the sheath 28 surrounds and is retained by the narrow end 54 of the support. For this purpose, the narrow end 54 of the support may further be fabricated with a groove (not shown) to retain the sheath on the narrow end of the support during storage. Preferably, the sheath 28 is rolled as stored on the support 50 such that the sheath is entirely positioned at the narrow end 54 of the support as stored. In this position, the closed end 31 of the sheath 28 covers the narrow aperture 56 of the support. As the head of the stethoscope is progressed through the narrow aperture of the narrow end, as shown in FIG. 4, and towards the large aperture 60, the closed end 31 of the sheath is elastically deformed and, upon reaching a certain state of deformation, it detaches from the support 50 and recoils to surround at least the head 12 of the stethoscope.

Figure 4:
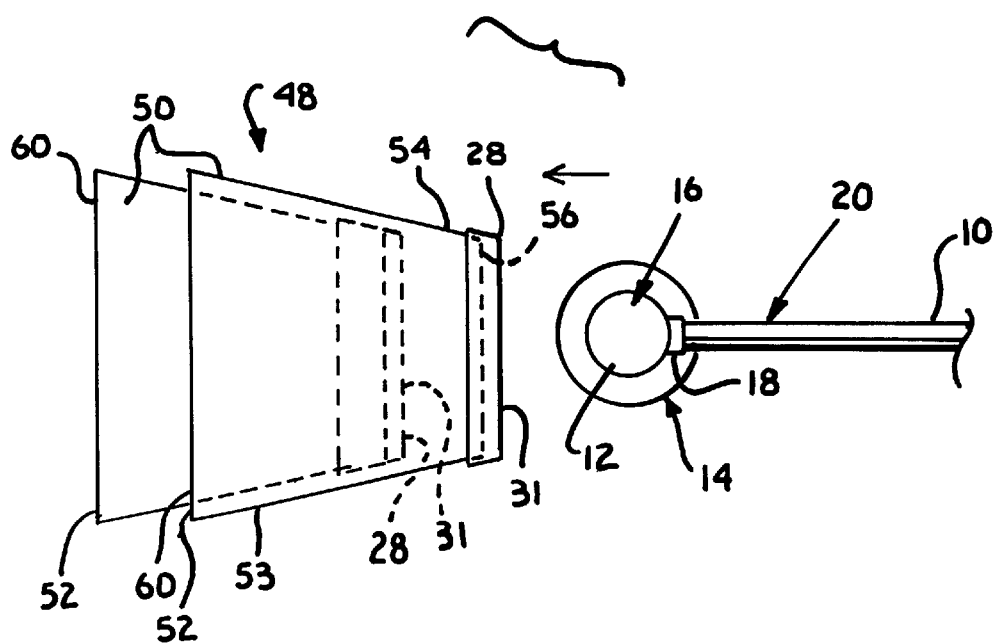
FIG. 4 is a frontal view of the sheath dispenser.

As shown in FIG. 4, the narrow end 54 of each support 50 is further sized such that it is mateable with the large end 58 of an other support thereby configuring the supports to be stackable. Preferable, the supports 50 are disposable and are made of a material that is sufficiently rigid to withstand the load of the elastically deformed sheath being mounted thereto. Cardboard or plastic materials may be used for the supports.

Use of a sheathing system of the present invention is simple. The retaining ring 32 is mounted to the sound tube 20 of the stethoscope by forcing the sound tube of the stethoscope through the channel 44 of the retaining ring into the interior of the ring. The sheath 28 is mounted to the stethoscope by forcing the head 12 of the stethoscope through the narrow aperture 56 of the support against the closed end 31 of the sheath. The closed end 31 of the sheath elastically deforms and thus pulls the sheath from the support. The elastically deformed sheath recoils and tautly surrounds the stethoscope head 12 and envelops the retaining ring. The support 50 that carried the sheath 28 is then disposed and the dispenser, which holds many supports with each support holding a sheath, is ready to mount the next sheath.

Alternatively, the sheath 28 is mounted directly to the stethoscope without the use of a retaining ring. In this embodiment the sheath is sized to tautly cover the head of the stethoscope and be retained on the stethoscope by the head. The sheath dispenser 48 permits the head of the stethoscope through the narrow end and the sheath detaches to envelop only the head portion of the stethoscope.

After using the stethoscope on a patient, a doctor or nurse may remove the sheath by simply stretching the sheath around the retaining ring and rolling the sleeve down off of the sound tube and head of the stethoscope. Perforations may be provided in the sleeve to facilitate removal.

The present invention allows a physician or nurse to use a high-quality stethoscope, without fear of contaminating it, and spreading the contaminated material to themselves or to other patients. This invention has particular application for use with very ill patients in intensive care units, patients with infectious diseases, patients who have open wounds or other sources of drainage of bodily fluids, or patients who are post-operative.

It will be understood that the embodiments of the invention described are merely illustrative of the application of the principles of the invention. Reference herein to details of the illustrated embodiment is not intended to limit the scope of the claims which themselves recite those features regarded as essential to the invention.

What is claimed is:

1. In combination, an elastic sheath for a stethoscope having a head, a sound tube and an earpiece, the sheath having an open end for admittance of the head and a portion of the sound tube and a closed end, the sheath being sized such that the head of the stethoscope and at least a portion of the sound tube is enveloped by the sheath, and a retaining ring mounted to the sound tube, the retaining ring extending radially outwardly from the sound tube and being sized such that the sheath plastically deforms to envelop the retaining ring such that the retaining ring releasably retains the sheath on the stethoscope.

2. The combination of claim 1, wherein the sheath is disposable.

3. The combination of claim 1, wherein the sheath is made from an acoustically permeable, biologically impermeable material.

4. In combination, a stethoscope having a head, a sound tube and an earpiece, a portion of the sound tube extending radially outwardly beyond the diameter of a remaining portion of the sound tube, and an elastic sheath having an open end for admittance of the head and the radially outwardly extending portion of the sound tube and a closed end, the sheath being sized such that the head of the stethoscope and at least the radially outwardly extending portion of the sound tube is enveloped by the sheath, the radially outwardly extending portion of the sound tube being sized such that the sheath plastically deforms to envelop the radially outwardly extending portion of the sound tube such that the radially outwardly extending portion releasably retains the sheath on the stethoscope.

5. The combination of claim 4, wherein the sheath is disposable.

6. The combination of claim 4, wherein the sheath is made from an acoustically permeable, biologically impermeable material.

7. A stethoscope sheath dispenser for mounting a sheath on a stethoscope having a head, a sound tube and an earpiece, the dispenser comprising, a plurality of supports, each support having an aperture defined therethrough sized such that at least the head of the stethoscope can progress through the aperture, and a plurality of elastic sheaths, each elastic sheath having an open end for admittance of the head and a closed end, the open end of each elastic sheath being elastically deformed to envelop a portion of a support and the closed end of each sheath being stretched to cover the aperture, whereby as the head of the stethoscope progresses through the aperture of the support, the sheath is detached from the support and recoils to surround at least the head of the stethoscope.

8. The stethoscope sheath dispenser of claim 7, wherein each support is frustroconically shaped and has a narrow end defining a narrow aperture and a large end defining a large aperture, the narrow aperture being sized such that the head of the stethoscope can progress therethrough, and wherein the elastic sheath is elastically deformed to surround the narrow end of each support.

9. The stethoscope sheath dispenser of claim 8, wherein the narrow end of each support of the plurality of supports is sized such that it is mateable with the large end of an other support of the plurality of support whereby the supports are stackable.

* * * * *